(12) United States Patent
Lenhard et al.

(10) Patent No.: US 10,024,803 B2
(45) Date of Patent: Jul. 17, 2018

(54) METHOD FOR DETERMINING AN ANALYTE IN AN AUTOMATED MANNER

(75) Inventors: Markus Lenhard, Viersen (DE); Manfred Battefeld, Duesseldorf (DE); Bernd Gassner, Neuss (DE); Baas De Heij, Dormagen (DE); Clemens Hanschke, Berlin (DE)

(73) Assignee: HACH LANGE GMBH, Berlin (DE)

( * ) Notice: Subject to any disclaimer, the term of this patent is extended or adjusted under 35 U.S.C. 154(b) by 21 days.

(21) Appl. No.: 13/825,553

(22) PCT Filed: Aug. 9, 2011

(86) PCT No.: PCT/EP2011/063692
§ 371 (c)(1),
(2), (4) Date: May 2, 2013

(87) PCT Pub. No.: WO2012/038146
PCT Pub. Date: Mar. 29, 2012

(65) Prior Publication Data
US 2013/0217141 A1     Aug. 22, 2013

(30) Foreign Application Priority Data
Sep. 23, 2010 (EP) .................................. 10178997

(51) Int. Cl.
*G01N 21/00* (2006.01)
*G01N 21/78* (2006.01)
(Continued)

(52) U.S. Cl.
CPC ............ *G01N 21/78* (2013.01); *B01L 3/5453* (2013.01); *G01N 35/00732* (2013.01);
(Continued)

(58) Field of Classification Search
CPC .................................................. B01L 2300/021
(Continued)

(56) References Cited

U.S. PATENT DOCUMENTS 5,386,287 A * 1/1995 Berssen et al. ............... 356/326
5,581,071 A * 12/1996 Chen et al. ............. 235/462.06
(Continued)

FOREIGN PATENT DOCUMENTS

| DE | 41 09 118 A1 | 9/1992 |
|---|---|---|
| WO | WO 2006/103083 A1 | 10/2006 |
| WO | WO 2007/086794 A1 | 8/2007 |

*Primary Examiner* — Christopher Hixson
*Assistant Examiner* — Emily R Berkeley
(74) *Attorney, Agent, or Firm* — Norman B. Thot

(57) ABSTRACT

A method for determining an analyte of a liquid sample in a cuvette includes providing a cuvette, a reagent, a barcode, an icon on the cuvette and a liquid analysis device comprising a photometer, a rotation device, a camera, a calibration data memory storing first calibration data, and an input device which manually inputs second calibration data. The cuvette is inserted into the liquid analysis device and is rotated to align the icon with the camera. The icon is read with the camera and the icon read compared with an icon model stored in the liquid analysis device to determine whether it corresponds thereto. The liquid sample is subjected to photometry based on the first calibration data if the icon read corresponds to the icon model. If not, the input apparatus is activated and the liquid sample is subjected to photometry on the basis of the second calibration data.

9 Claims, 2 Drawing Sheets

(51) Int. Cl.
*B01L 3/00* (2006.01)
*G01N 35/00* (2006.01)
(52) U.S. Cl.
CPC ... *B01L 2200/148* (2013.01); *B01L 2300/021* (2013.01); *G01N 2035/00752* (2013.01); *G01N 2035/00772* (2013.01); *G01N 2035/00851* (2013.01)
(58) Field of Classification Search
USPC .......................................................... 436/164
See application file for complete search history.

(56) References Cited

U.S. PATENT DOCUMENTS

| | | |
|---|---|---|
| 7,303,139 B1 * | 12/2007 | Rudloff .................. 235/494 |
| 2002/0009395 A1 * | 1/2002 | Hirono et al. .................. 422/67 |
| 2004/0086173 A1 | 5/2004 | Itoh |
| 2005/0205673 A1 * | 9/2005 | Morris .................. B01L 3/5027 235/385 |
| 2005/0279647 A1 | 12/2005 | Beaty |
| 2006/0038016 A1 * | 2/2006 | Tangezaka et al. ...... 235/462.06 |
| 2008/0021436 A1 * | 1/2008 | Wolpert et al. ............... 604/504 |
| 2008/0254544 A1 | 10/2008 | Modzelewski et al. |
| 2008/0317326 A1 | 12/2008 | Svanberg et al. |
| 2009/0119024 A1 * | 5/2009 | Pritchard ........... A61B 5/14532 702/23 |

\* cited by examiner

METHOD FOR DETERMINING AN ANALYTE IN AN AUTOMATED MANNER

CROSS REFERENCE TO PRIOR APPLICATIONS

This application is a U.S. National Phase application under 35 U.S.C. § 371 of International Application No. PCT/EP2011/063692, filed on Aug. 9, 2011 and which claims benefit to European Patent Application No. 10178997.2, filed on Sep. 23, 2010. The International Application was published in German on Mar. 29, 2012 as WO 2012/038146 A1 under PCT Article 21(2).

FIELD

The present invention relates to a method for the automated determination of an analyte in a liquid sample in a circular cuvette in a liquid analysis device.

BACKGROUND

The present invention relates to the determination of an analyte in a water sample. Such a method is described in DE 41 09 118 A1 where the cuvette has a one-dimensional barcode that contains information on the analyte to be determined. A cuvette is a vessel suitable for photometry which is transparent for the measuring radiation and into which the liquid sample is introduced and in which it is mixed with the reagent. The liquid analysis device comprises a rotation device with which the cuvette placed in the liquid analysis device can be rotated. The rotation device rotates the cuvette both while the barcode provided on the cuvette is read in the longitudinal direction and during photometry.

For an accurate quantitative determination of the analyte, the measuring signals acquired by the photometer must be converted into corresponding quantity measuring values using calibration data assigned to the respective analyte.

SUMMARY

An aspect of the present invention is to provide a method for the quantitative determination of an analyte of a liquid sample in a liquid analysis device in which an error-free use of the calibration data is provided.

In an embodiment, the present invention provides a method for automatically determining an analyte of a liquid sample in a cuvette in a liquid analysis device which includes providing a cuvette which is configured to be cylindrical. A reagent which is configured to react with the analyte in a color-changing manner is provided. A barcode configured either as a one-dimensional barcode or as a two-dimensional barcode is provided. An icon with two dimensions is provided on an outside of the cuvette. A liquid analysis device is provided which comprises a photometer, a rotation device which is configured to rotate a cuvette inserted in the liquid analysis device, a camera which is configured to read the barcode and the icon, a calibration data memory which is configured to store first calibration data associated with the reagent, and an input device which is configured to manually input second calibration data associated with the reagent. The cuvette is inserted into the liquid analysis device. The cuvette is rotated so as to align the icon with the camera. The icon is read with the camera. The icon read is compared with an icon model stored in the liquid analysis device. It is determined whether the icon read corresponds to the icon model. The liquid sample is subjected to photometry on the basis of the first calibration data stored in the calibration data memory if the icon read corresponds to the icon model. The input apparatus for manually inputting the second calibration data is activated if the icon read does not correspond to the icon model. The liquid sample is subjected to photometry on the basis of the second calibration data which has been manually input.

BRIEF DESCRIPTION OF THE DRAWINGS

The present invention is described in greater detail below on the basis of embodiments and of the drawings in which.

DETAILED DESCRIPTION

Figure 1:
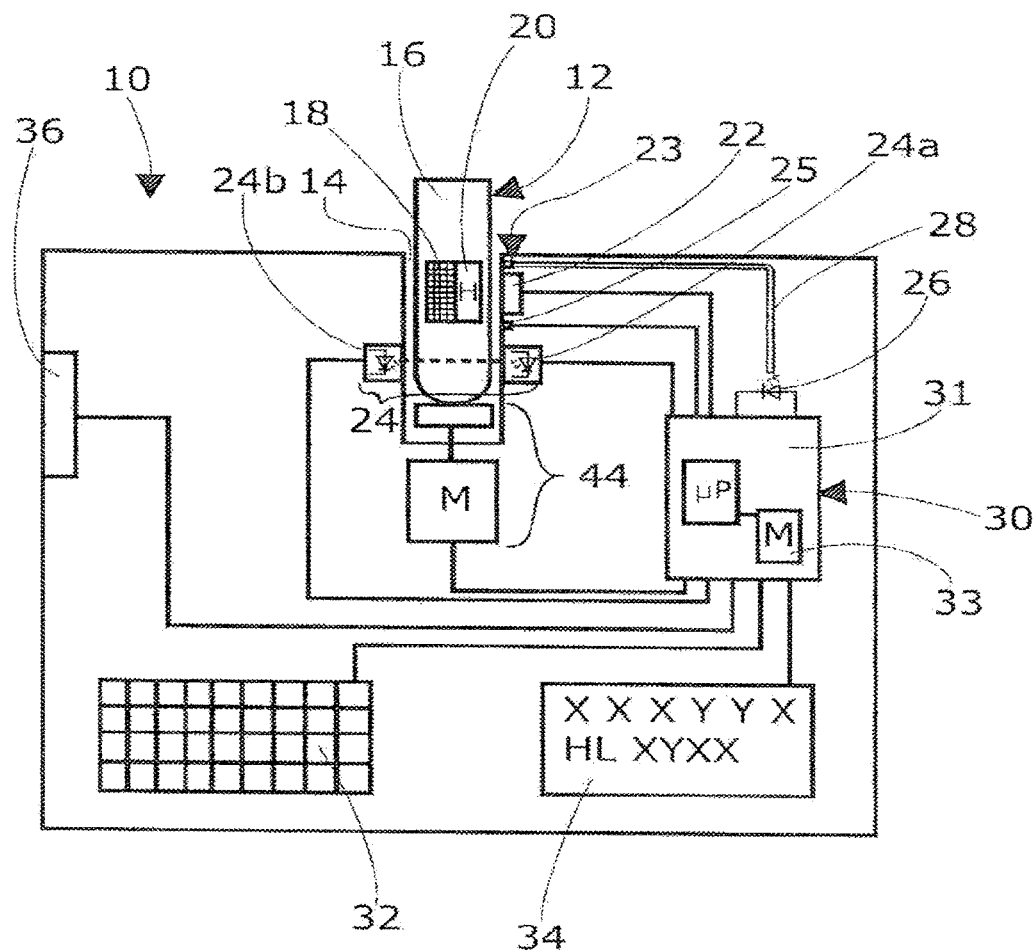
FIG. 1 shows a schematic illustration of a liquid analysis device for the execution of the method according to the present invention.

The method of the present invention relates to the automated determination of an analyte of a liquid sample in a circular or cylindrical cuvette in the liquid analysis device. The cuvette contains a reagent that reacts with the analyte in a color-changing manner. The cuvette also has a one- or a two-dimensional barcode and a separate two-dimensional icon on the cuvette outer side. The icon could be a trademark, a brand, a mark or another two-dimensional identification of the manufacturer or supplier of the cuvette containing the reagent.

Besides a photometer and a rotation device for rotating the inserted cuvette, the liquid analysis device comprises a line-scan or area-scan camera for reading the barcode and the icon. It is generally advantageous to provide a single camera for reading the barcode and the icon. It is also generally possible, however, to provide two separate cameras for this purpose. The liquid analysis device also comprises an electronic calibration data memory for storing the calibration data of a batch of a reagent. A reagent batch is to be understood, for example, as the entirety of all cuvettes filled with a reagent having identical calibration data.

The liquid analysis device also comprises an electronic memory for storing an icon model. The liquid analysis device finally comprises an input device for the manual entry of reagent calibration data. The input device may, for example, be a keyboard, a key, a knob, a touch screen or another manual input device.

According to the method of the present invention, the cuvette inserted into the liquid analysis device is rotated by the rotation device, whereby the icon is rotationally aligned with the camera such that the icon can be read by the camera as a photo into the liquid analysis device. The icon photo read is thereafter compared with the stored icon model. If the icon photo does not correspond to the stored icon model, the input device for the manual entry of the calibration data is activated and, if need be, the operator is prompted to manually enter the calibration data. After the calibration data has been entered manually, the liquid sample is subjected to photometry and the measuring signal is converted into a corresponding measured value using the calibration data entered.

If the icon photo corresponds to the stored icon model within a fixed tolerance, the measuring signal of the photometry is converted into a corresponding measured value using the calibration data stored in the calibration data memory.

The calibration data from the calibration data memory is thus used to determine the measured value only if the cuvette bears the icon of the cuvette manufacturer or supplier. It is thereby provided that when cuvettes of a third party manufacturer or supplier are used, that the calibration data of the original manufacturer or supplier, which would inevitably lead to incorrect measured values, are not used. An error-free use of calibration data is thereby provided during the determination of a measured value.

In an embodiment of the present invention, the barcode may, for example, include an analyte batch identification, where, first, the batch identification on the barcode of the inserted cuvette is read using the camera, and, thereafter, it is checked whether calibration data is already stored in the calibration data memory for the batch identification read by the camera. If calibration data is already stored in the calibration data memory for the batch identification read, the photometry of the liquid sample is continued.

If, however, no calibration data is stored in the calibration data memory for the batch identification read, a prompt for reading in the calibration data for the new batch identification is outputted. Reading in the calibration data can be effected, for example, by holding a RFID label, which stores the calibration data of the respective batch identification, to a corresponding reader of the liquid analysis device, wherein the reader automatically reads the corresponding calibration data from the RFID label and (assigned to the respective batch identification) stores them in the calibration data memory.

In an alternative or complementary embodiment of the present invention, the barcode can, for example, include the calibration data of the respective cuvette or batch, wherein the barcode with the calibration data is read using the camera and the calibration data is finally stored in the calibration data memory. Reading the calibration data from the barcode can be undertaken for each measurement, it can, alternatively, be performed only when a cuvette of a new batch is inserted into the liquid analysis device for which no calibration data is yet stored in the calibration data memory.

In an embodiment of the present invention, in all cuvettes, the barcode and the icon can, for example, have a fixed geometric relation with respect to each other, wherein the camera first determines the rotational and possibly the vertical position of the barcode on the cuvette, and then the position of the icon is determined from the position of the barcode using the known geometric relation. Since the position of the icon on the cuvette is known from the position of the barcode, it is no longer necessary to search for the icon on the cuvette, but the rotation device can rotate the icon on the cuvette to a position exactly in front of the camera so that the overall icon reading process can be performed in a time-saving manner.

In an embodiment of the present invention, the liquid analysis device can, for example, comprise a lighting device with a light source for illuminating the icon on the cuvette. Due to the illumination of the cuvette, the useful signal of the camera becomes larger so that the quality of the icon photo is improved. The shutter speed of the camera can also be correspondingly reduced so that a photo of the icon could possibly be taken even during a rotary movement of the cuvette.

In an embodiment of the present invention, the lighting device or the light source of the lighting device can, for example, be operated in a pulsed manner. In pulsed operation, the lighting device or the light source can temporarily supply a significantly higher light output than in continuous operation. The shutter speed of the camera is also thereby reduced in a corresponding manner.

In an embodiment of the present invention, the lighting device can, for example, include an optical light guide that guides the light from the light source to the cuvette inserted. The light source, such as a light emitting diode, may be arranged on a mainboard that comprises the entire electronics of the liquid analysis device. No separate circuit board is required for the light source and its control. The light is guided from the light source on the mainboard through the optical light guide to the cuvette shaft and to the vicinity of the camera.

In an embodiment of the present invention, the lighting device can, for example, have a brightness sensor and a brightness control. The brightness sensor is fastened to the cuvette shaft and is spatially positioned with respect to the barcode and the icon on the cuvette inserted such that the brightness sensor detects the brightness of the light reflected from the barcode and the icon, i.e., of the useful signal for the camera. The output of the light source is controlled by means of the brightness control such that the contrast of the useful signal received by the camera is optimally set.

The following is a detailed description of the method of the present invention with reference to the drawings.

FIG. 1 illustrates a liquid analysis device 10 with a cuvette 12 inserted in a cuvette shaft 14. The liquid analysis device 10 is a so-called laboratory apparatus and serves to analyze various photometrically determinable analytes in water, such as in waste water, treated waste water or potable water.

Figure 2:
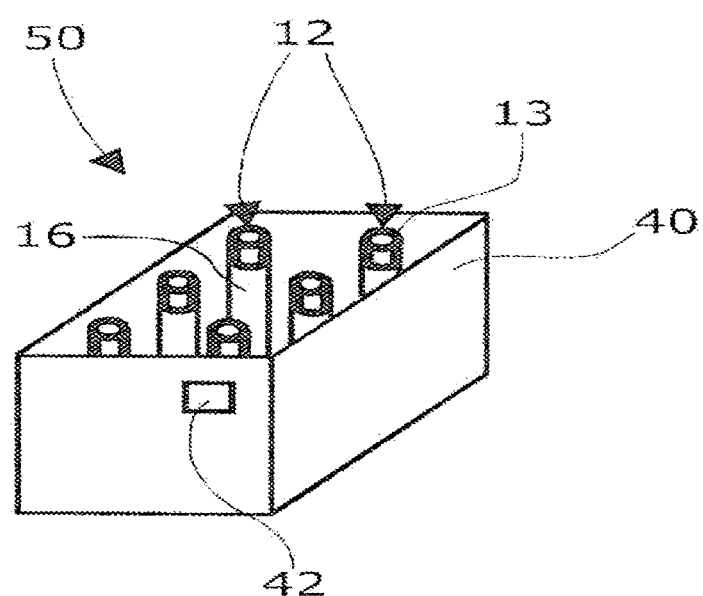
FIG. 2 shows a cuvette container with a RFID label and a plurality of cuvettes of a batch.

The cuvette 12 is formed by a cylindrical glass body 16 comprising a two-dimensional barcode 18 stuck thereon and a two-dimensional icon 20 adjoining the barcode 18 in the circumferential direction. The cuvette manufacturer has filled the glass body 16 with a reagent in a defined amount, concentration and quality, which reagent serves to determine a specific analyte in a liquid sample. The cuvette 12 is thus composed of the glass body 16, the barcode 18, the icon 20 and the reagent. When not in use, the cuvette 12 closed with a liquid-tight screw cap 13, as can be seen in FIG. 2.

The barcode 18 includes encoded information about the type of test, i.e., information about the analyte that can be determined with the reagent, information about the manufacture and shelf-life, as well as a batch identification which is the same for all cuvettes of a batch. A cuvette batch is entirely homogeneous with respect to the reagent. A cuvette batch has assigned thereto a single set of calibration data that serve to accurately calculate, from a photometric measuring signal, an exact quantitative measured value for the analyte to be determined.

The icon 20 may, for example, be a product or manufacturer identification that is identical for all cuvettes of a manufacturer, and it may, although not necessarily, also include a verbal component. The icon 20 should have a maximum possible contrast, for example, it may be only black and white.

The barcode 18 and the icon 20 are applied on the glass body 16 at such a height that, with the cuvette 12 inserted in the cuvette shaft 14, they are arranged within the cuvette shaft 14, with respect to their vertical position, and that they are radially aligned with a camera 22 provided on the wall of the cuvette shaft 14. The barcode 18 and the icon 20 are arranged geometrically with a fixed constant relation to each other. It is thereby possible to conclude the exact position of the icon 20 from the position of the barcode 18 which must first be found and read by the camera 22. The icon 20 thus does not have to be searched for, but can be aligned directly with the camera 22 by the rotation device 44.

The camera 22 is a vertically orientated line camera having a resolution of, for example, 320 pixels. As an alternative, the camera 22 may also be configured as an area camera. In this case, corresponding rectifications of the camera photos would have to be made for an evaluation of the camera photos.

A photometer 24 is positioned below the camera 22, which is formed by a photometer transmitter 24a and a photometer receiver 24b. The photometer 24 serves to photometrically determine the analyte of a liquid sample pipetted into the cuvette 16, which sample reacts with the reagent in the cuvette 16 in a color-changing manner in a specific spectral range. The modification of the transmission in the respective spectral range is determined by the photometer 24 in the form of a measuring signal that is transmitted to a device control 30.

The liquid analysis device 10 comprises a rotation device 44 with a turntable, by which the cuvette 12 inserted into the cuvette shaft 14 can be rotated around the longitudinal axis of the cuvette in a defined, step-wise manner.

The liquid analysis device 10 includes a lighting device 23 mounted on the wall of the cuvette shaft 14 which is spatially associated with the camera 22, and which illuminates the barcode 18 and the icon 20 on the glass body 16, if necessary. The lighting device 23 is formed by a LED light source 26 arranged on a mainboard 31 of the device control 30, and an optical light guide 28 of plastic material guiding the light of the light source 26 to the cuvette shaft 14. In operation, the light source is pulsed so as to avoid an overheating of the light source 26 by a temporarily high light output.

The liquid analysis device 10 comprises a manual input device 32 in the form of a keyboard and a display device 34 in the form of a monitor. The liquid analysis device 10 further comprises a RFID transceiver 36 that is able to read calibration data from a RFID label 42 on the cuvette package body 40.

The drive control 30 comprises a calibration data memory 33, in which the calibration data of a cuvette batch or of a plurality of cuvette batches are stored.

FIG. 2 illustrates a cuvette package unit 50 comprising a cuvette package body 40, a plurality of cuvettes 12 of a batch and a RFID label 42 with calibration data of the respective cuvette batch.

The method for the automated determination of an analyte in a liquid sample is executed as follows:

First, a cuvette 12 is taken from the cuvette package body 40 and the screw cap 13 is unscrewed from the cuvette glass body 16. A pipette is then used to introduce a defined volume of a liquid sample into the cuvette 12. The analyte to be determined in the liquid sample reacts with the reagent in the cuvette 12 in a color-changing manner. The cuvette 12 is next inserted into the cuvette shaft 14, with the photometer 24 determining a sudden reduction in transmission, whereby a measuring cycle is triggered.

The device control 30 then causes the activation of the lighting device 23 and the turning of the cuvette 12 by the rotation device 44 so as to align the barcode 18 with the camera 22. The camera 22 takes a photo of the barcode 18 which is evaluated and read by the device control 30. The output of the light source 26 is controlled using the brightness sensor 25 such that the barcode photo has an optimal contrast. After the camera 22 has taken the barcode photo, the rotation device 44 turns the cuvette 12 through a known differential rotation angle so that the icon 20 is aligned with the camera 22.

The icon 20 is read by the camera 22, that is, the camera 22 takes a photo of the icon. The device control 30 compares the icon photo with a permanently stored icon model and continues with the batch identification if the icon photo corresponds to the icon model. Here, the batch identification of the inserted cuvette 12 is determined from the barcode 18 read. The photometry is continued if the calibration data memory 33 has already stored the calibration data of this batch identification.

If no calibration data is stored for this batch identification in the calibration data memory 33, the operator is prompted by an acoustic signal and via the display device 34 to read in the calibration data for this batch identification. This is done by holding the RFID label 42 on the cuvette package body 40 immediately in front of the RFID transceiver of the liquid analysis device 10. As soon as a radio link is established between the RFID label 42 and the RFID transceiver, the calibration data of this cuvette batch is transferred to the calibration data memory 33 and is stored therein. The photometry is thereafter continued.

If the icon photo does not correspond to the icon model, the operator is prompted by the display device 34 to enter the calibration data manually via input device 32. The photometry is continued as soon as the calibration data has been entered by the operator via input device 32.

For photometry purposes, the device control 30 activates the photometer 24, whereby the rotation device 44 turns the cuvette 12 in intervals so that a plurality of measurements can be made at various rotation angles of the cuvette 12. The plurality of measuring signals thus acquired by the photometer 24 are converted into corresponding measured values in the device control using the calibration data stored in or manually entered into the calibration data memory 33, which values indicate the concentration of the analyte in the liquid sample. So-called runaway values are cancelled from the plurality of measured values and an average value is generated from the remaining measured values, which is displayed on the display device 34.

The present invention is not limited to embodiments described herein; reference should be had to the appended claims.

What is claimed is:

1. A method for automatically determining an analyte of a liquid sample in a cuvette in a liquid analysis device, the method comprising:
   providing a cuvette package comprising,
      a batch of cuvettes arranged in the cuvette package, each of the cuvette being cylindrical and containing a reagent which reacts with the analyte in a color-changing manner, and
      an RFID label arranged on the cuvette package, the RFID label storing first calibration data associated with the reagent;
   applying a barcode configured either as a one-dimensional barcode or as a two-dimensional barcode to a cuvette of the batch of cuvettes;
   applying an icon with two dimensions to the cuvette;
   providing a liquid analysis device comprising:
      a photometer,
      a cuvette rotator which rotates a cuvette inserted in the liquid analysis device,
      a camera which is configured to read the barcode and the icon,
      a calibration data memory which stores first calibration data associated with the reagent, an input means via which a user can manually input second calibration data associated with the reagent, and an RFID transceiver which can read the first calibration data stored in the RFID label;

inserting the cuvette into the liquid analysis device;

rotating the cuvette so as to align the icon with the camera;

reading the icon with the camera;

comparing the icon read with an icon model stored in the liquid analysis device;

determining whether the icon read corresponds to the icon model; and if the icon read is determined to correspond to the icon model and if first calibration data is stored in the calibration data memory, subjecting the liquid sample to photometry on the basis of the first calibration data stored in the calibration data memory, or, if the icon read is determined to correspond to the icon model and if no first calibration data is stored in the calibration data memory, holding the RFID label arranged on the cuvette package in front of the RFID transceiver of the liquid analysis device so as to establish a radio link between the RFID label and the RFID transceiver and to thereby transfer the first calibration data for the batch of cuvettes to the calibration data memory, and subjecting the liquid sample to photometry on the basis of the first calibration data stored in the calibration data memory, or, if the icon read is determined to not correspond to the icon model, activating the input means so that the second calibration data can be manually input by the user; and, after the second calibration data has been input by the user, subjecting the liquid sample to photometry on the basis of the second calibration data which has been manually input by the user, wherein, the first calibration data or the second calibration data is used to convert the measuring signals acquired by the photometer into corresponding quantity measuring values so as to obtain an accurate quantitative determination of the analyte.

2. The method as recited in claim 1, wherein the camera is at least one of a line scan camera and an area scan camera.

3. The method as recited in claim 1, wherein the barcode includes first calibration data, and the method further comprises:

reading the first calibration data on the barcode with the camera; and storing the first calibration data read in the calibration data memory.

4. The method as recited in claim 3, wherein the barcode comprises an analyte batch identification, and the method further comprises:

reading the analyte batch identification on the barcode;

checking whether first calibration data is stored in the calibration data memory for the analyte batch identification read; and outputting a prompt to read-in the first calibration data for a new batch identification if no first calibration data is stored for the analyte charge identification read.

5. The method as recited in claim 1, wherein the barcode and the icon are provided in a fixed relation relative to each other on the cuvette, and the method further comprises:

determining a rotational position of the barcode on the cuvette with the camera; and calculating a position of the icon on the cuvette from the rotational position of the barcode.

6. The method as recited in claim 1, wherein the liquid analysis device further comprises a lighting device which is configured to illuminate at least one of the barcode and the icon on the cuvette, and the method further comprises:

illuminating the cuvette while reading at least one of the barcode and the icon.

7. The method as recited in claim 6, wherein the lighting device is operated in a pulsed manner.

8. The method as recited in claim 6, wherein the lighting device comprises an optical light guide which is configured to guide a light from a light source to the cuvette.

9. The method as recited in claim 8, wherein the lighting device comprises a brightness control and a brightness sensor which is spatially associated with the barcode and the icon of the cuvette, the brightness sensor being configured to measure a brightness, and the method further comprises:

controlling a light output of the light source as a function of the brightness measured by the brightness sensor.

* * * * *